United States Patent
McGrath

(10) Patent No.: US 11,101,805 B2
(45) Date of Patent: Aug. 24, 2021

(54) PRESCRIPTION ADHERENCE ASSISTANCE

(71) Applicant: EXPERIAN HEALTH, INC, Franklin, TN (US)

(72) Inventor: Matthew McGrath, Cumming, GA (US)

(73) Assignee: Experian Health, Inc., Franklin, TN (US)

( * ) Notice: Subject to any disclaimer, the term of this patent is extended or adjusted under 35 U.S.C. 154(b) by 1347 days.

(21) Appl. No.: 15/063,451

(22) Filed: Mar. 7, 2016

(65) Prior Publication Data
US 2017/0255759 A1   Sep. 7, 2017

(51) Int. Cl.
*H03K 19/20*   (2006.01)
*H03K 19/21*   (2006.01)
*G16H 20/10*   (2018.01)

(52) U.S. Cl.
CPC .............. *H03K 19/20* (2013.01); *G16H 20/10* (2018.01); *H03K 19/21* (2013.01)

(58) Field of Classification Search
CPC ........ H03K 19/20; H03K 19/21; G06Q 10/10; G06Q 40/08; G06Q 50/22; G16H 10/60; G16H 20/10; G16H 40/20; G06F 19/328
USPC ....................................................... 705/2–3
See application file for complete search history.

(56) References Cited

U.S. PATENT DOCUMENTS

| | | | |
|---|---|---|---|
| 2004/0073457 A1* | 4/2004 | Kalies | G06Q 20/28 705/2 |
| 2004/0153336 A1* | 8/2004 | Virdee | G06Q 40/08 705/2 |
| 2007/0061393 A1* | 3/2007 | Moore | G06Q 10/10 709/201 |
| 2008/0033750 A1* | 2/2008 | Burriss | G06Q 10/10 705/2 |
| 2012/0123789 A1* | 5/2012 | Patel | G16H 40/20 705/2 |

OTHER PUBLICATIONS

PayingForSeniorCare.com, Pharmaceutical Patient Assistance Programs: Lowering the Cost of Medications, Apr. 14, 2009, http://payingforseniorcare.com/patient-assistance-programs (Year: 2009).*

* cited by examiner

*Primary Examiner* — Joy Chng
(74) *Attorney, Agent, or Firm* — Knobbe, Martens, Olson & Bear, LLP

(57) ABSTRACT

Improvements to the process of providing patient assistance to conform with prescribed courses of treatment are provided. Providing assistance based on patient-specific data is implemented via an assistance analyzer communicated with a processing clearinghouse, and the process of determining how to assist the patients in adhering to their courses of treatment at the time the prescription is filled, without the patient engaging in a separate process to apply for a discount. By applying the present disclosure, existing systems improve their sensitivity to patient need when providing time sensitive information, and may be configured to use fewer processing resources than before; improving the functionality of the systems themselves.

18 Claims, 5 Drawing Sheets

PRESCRIPTION ADHERENCE ASSISTANCE

BACKGROUND

Patients who are issued prescriptions for treatment by their healthcare providers, including prescriptions for medications and for devices, rarely pay the list price for the prescribed treatment; health insurance and coupon programs serve to insulate patients from the full cost of prescriptions. Manufacturers of therapeutics (pharmaceutical compounds and medical devices) currently attempt to establish a target copay amount for patients via coupon programs used in conjunction with any health insurance that a patient may have. The target copay amount is selected based on aggregated prescription fulfillment and abandonment rates to increase the attractiveness of a given therapeutic to the average patient. For example, a manufacturer may determine that once a copay exceeds $50 for a given prescription, there is a significant increase in patients foregoing or abandoning the therapeutic in favor of an alternative therapeutic or no therapeutic, and therefore a coupon program would be implemented to reduce the cost of the prescription to the patient (in addition to any insurance coverage) to encourage adherence to the prescribed course of treatment. However, these coupon programs are based on the average patient, and a particular patient may need more (or less) assistance to reach a point where the therapeutic is affordable and the patient is able to adhere to the treatment as prescribed.

SUMMARY

The present disclosure provides systems and methods for improving the functionality of systems used for assisting patients to access affordable treatments. The systems and methods described herein assist patients in adhering to their courses of treatment by improving the prescription filling process to use patient-specific data. These data enable healthcare providers to prescribe preferred therapeutics, with reduced worry that their patients will deviate from treatment due to issues of affordability, and for the patients to quickly receive a tailored discount for those therapeutics. The systems and methods used to assist patients work in conjunction with pharmacy and prescription benefit manger (PBM) systems to provide the discount at the time the prescription is filled, without the patient engaging in a separate process to apply for a discount. By applying the present disclosure, existing systems improve their sensitivity to patient need when providing time sensitive information, and may be configured to use fewer processing resources than before; improving the functionality of the systems themselves.

Aspects of systems and methods described herein may be practiced in hardware implementations, software implementations, and in combined hardware/software implementation. This summary is provided to introduce a selection of concepts; it is not intended to identify all features or limit the scope of the claimed subject matter.

BRIEF DESCRIPTION OF THE DRAWINGS

The accompanying drawings, which are incorporated in and constitute a part of this disclosure, illustrate various aspects and examples of the present invention. In the drawings.

DETAILED DESCRIPTION

Figure 1:
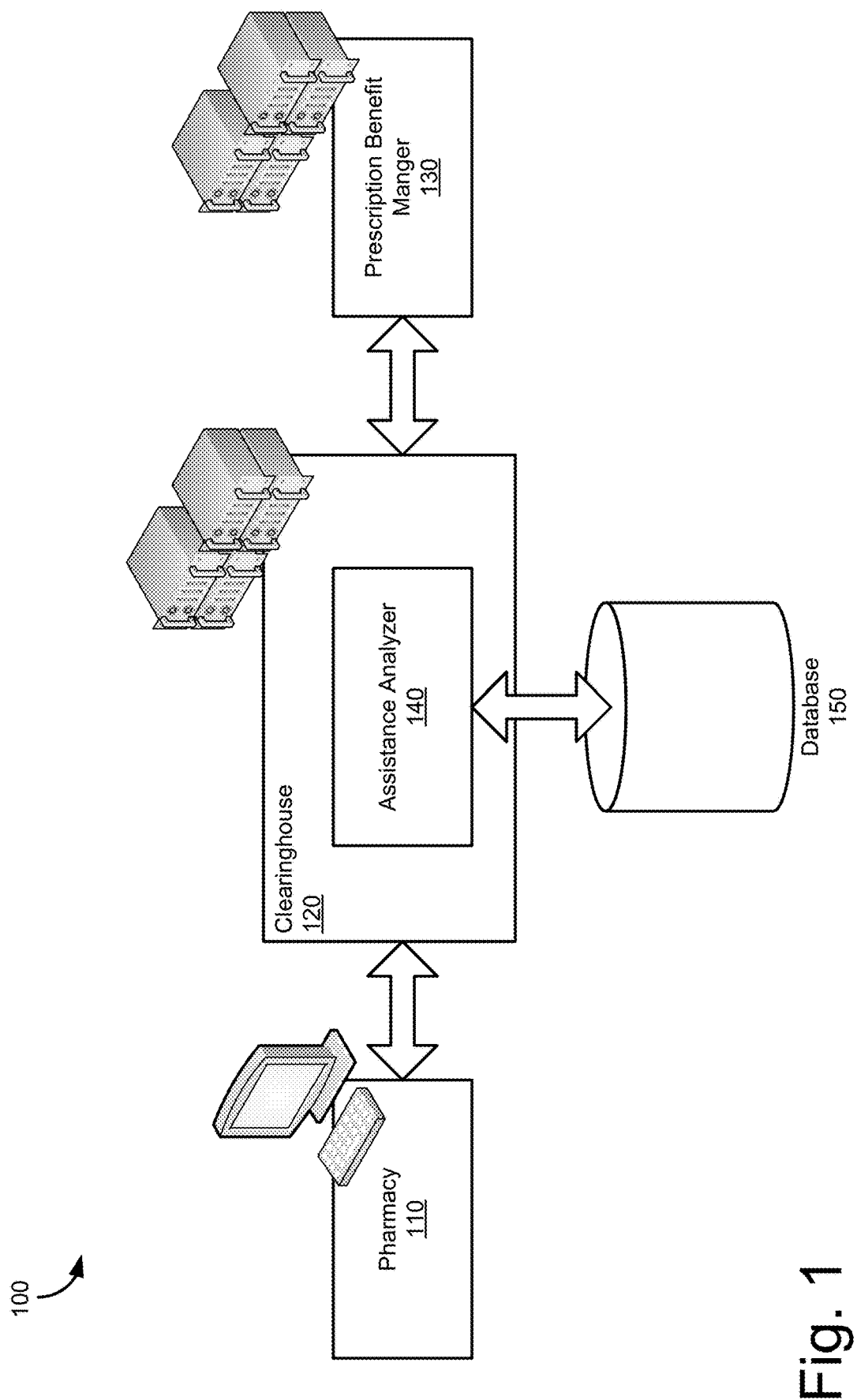
FIG. 1 is a block diagram of an example environment in which prescription adherence assistance may be practiced.

The following detailed description refers to the accompanying drawings. Wherever possible, the same reference numbers are used in the drawings and the following description to refer to the same or similar elements. While aspects of the present disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the present disclosure, but instead, the proper scope of the present disclosure is defined by the appended claims. Examples may take the form of a hardware implementation, or an entirely software implementation, or an implementation combining software and hardware aspects. The following detailed description is, therefore, not to be taken in a limiting sense.

Ensuring that patients are able to adhere to their respective courses of treatment is a significant challenge for healthcare providers. Once patients have been discharged from a healthcare provider's care, their continued adherence to a treatment plan is in their own hands (or the hands of a, hopefully, responsible guardian). Patients, however, often stray from adherence to a course of treatment, and one of the largest factors is the prolonged cost of some therapeutics. Patients are known to vary the dosages of medications, stop treatment prematurely, and use over the counter (OTC) "substitutes" instead of therapeutics as prescribed.

Healthcare providers, in response to the issues associated with the affordability of some therapeutics, have been known to adjust their prescribing patterns to ensure that their patients will adhere to a course of treatment as prescribed. For example, a healthcare provider may provide a patient with "sample" therapeutics, give the patient one or more paper coupons for discounts on the therapeutic, break the prescription into smaller amounts (e.g., two prescriptions for a thirty day supply versus one for a sixty day supply), or, more ominously, prescribe a therapeutic of secondary choice based on its lower cost. Healthcare providers, conscious of the fact that full compliance to treatment with a therapeutic of lower efficacy may be preferable to non-compliance to treatment with a preferred therapeutic, may give prescriptions based on the affordability of the therapeutics prescribed instead of the efficacy of those therapeutics.

The manufacturers and distributors of therapeutics (collectively, manufacturers) are aware of these trends, and for certain therapeutics offer copay discount programs to reduce the out-of-pocket expense to patients when prescriptions are filled. These programs set a "target" copay based on aggregate data and estimates of compliance points. The compliance points are the expected point where the average patient will be expected to continue treatment as prescribed, rather that forgo or ration treatment. For example, for a target copay of $50, a patient whose insurance provides the therapeutic with a copay of $45 will not receive a discount, whereas a patient whose insurance provides the therapeutic with a copay of $55 will receive a discount of $5. These programs are applied at the time a prescription is filled, however, they may be capped (e.g., a maximum size of a discount may not be enough to reduce the out of pocket expense to the target amount) and do not take into account patient-specific factors, such as, for example: income, age, credit history, veteran status, employment, participation in a medical study, etc.

Systems that take into account patient-specific factors to increase the availability of therapeutics and improve adherence thereto are applied separately from filling the prescriptions, and are often burdensome. For example, in a discount system from the manufacturer based on their patient-specific factors, a patient may buy an expensive treatment (e.g., chemotherapy) and then seek the discount, or seek the discount before filling the prescription for the therapy. Both of these approaches place burdens on the patient, who may not be able to financially afford the initial payment, and who may not be able to physically afford to delay the initial treatment.

The systems and methods described herein assist patients in adhering to their courses of treatment by improving the prescription filling process to use patient-specific data. These data enable healthcare providers to prescribe preferred therapeutics, with reduced worry that their patients will deviate from treatment due to issues of affordability, and for the patients to quickly receive a tailored discount for those therapeutics. The systems and methods used to assist patients work in conjunction with pharmacy and prescription benefit manger (PBM) systems to provide the discount at the time the prescription is filled, without the patient engaging in a separate process to apply for a discount. By applying the present disclosure, existing systems improve their sensitivity to patient need when providing time sensitive information, and may be configured to use fewer processing resources than before; improving the functionality of the systems themselves.

As used herein, the term "therapeutic," when used as a noun, refers to medications, substances, and devices set forth in a prescription for the treatment of (or relief from) a medical condition. To illustrate: an antibiotic, a blood thinning medication, an opioid pain reliever, oxygen, contact lenses, and a knee brace are all non-limiting examples of potential therapeutics.

Examples of numbers in the present disclosure are given in base ten unless noted otherwise. When a different base is used, a subscript beginning with the character "x" and the base value (in base ten) will follow the number. For example, the number ten may be designated as 10, $A_{x16}$, or $1010_{x2}$ for decimal, hexadecimal, and binary examples respectively. Additionally, for numbers given in binary formats, numbers will be presented in groups of four with spaces between each group. For example, in binary, the number one is presented as $0001_{x2}$ and the number seventeen is presented as $0001\ 0001_{x2}$. When individual values for bits are discussed, they may be represented as "one/TRUE" or "zero/FALSE" to distinguish these values within the text. One of ordinary skill in the art will be able to read and understand these values within the context that they are given in the present disclosure.

FIG. 1 is a block diagram of an example environment 100 in which prescription adherence assistance may be practiced. In the illustrated environment 100, a clearinghouse 120 is in communication with a pharmacy 110, a PBM 130, and a database 150 to help process payments for pharmacy transactions. The clearinghouse 120 also includes an assistance analyzer 140, which is operable to determine when and how a particular patient is to be assisted for the procurement of therapeutics, to assist the patient in adhering to a course of treatment. As will be appreciated, although only one pharmacy 110, PBM 130, and database 150 are illustrated in communication with the clearinghouse 120, a greater number of each may be in communication with the clearinghouse 120 than illustrated in FIG. 1.

Each of the pharmacy 110, clearinghouse 120, and PBM 130 are illustrated as computer systems in communication with one another. For example, the pharmacy 110 may include a computer system used by a pharmacist to enter data to fulfill a prescription for a patient as part of a pharmacy practice management system, the clearinghouse 120 may include a server for processing prescription requests, and the PBM 130 may include a server for providing coverage information, for example from an insurer or prescription discount program. The database 150 may be a standalone device comprising computer readable storage media or part of a computing device used by a third-party, such as, for example, a credit bureau, an assisted living center, a different pharmacy, a government database, etc.

Each of the pharmacy 110, clearinghouse 120, and PBM 130 may be in communication with each other via a distributed network, such as, for example, the Internet, or via a direct data link. Similarly, the database 150 may be in communication with the clearinghouse 120 via a distributed network or direct data link, if the database 150 is located remotely from the clearinghouse 120, or via a private network or direct data link, if the database 150 is located locally to the clearinghouse 120. Communications between the systems may be encrypted or conducted via a Virtual Private Network (VPN), and may comprise structured communications that conform to various standards and formats. For example, a National Council for Prescription Drug Programs (NCPDP) standard for pharmacy transactions.

The structured communications include data in known formats and locations within an electronic communication. For example, a Bank Identification Number (BIN) may be known to include a four-to-six digit number at position X within the communication that identifies a payor. Similarly, a Processor Controller Number (PCN), used for routing pharmacy transactions to an indicated PBM 130 to process and pay prescription claims may be located at position Y within the communication. The exact position and expected size of data in the structured communications may vary based on the standard used, and how those data are encoded may also vary. For example, information may be encoded as characters via a Unicode Transformation Format (UTF), such as UTF-8, UTF-16, UTF-32, etc., the American Standard Code for Information Interchange (ASCII), or another character encoding scheme. Information may be included in a human readable format or encoded, for example, via an ICD-10 (International Statistical Classification of Diseases and Related Health Problems, version ten) code, an NDC (National Drug Code) code, an ATC (Anatomical Therapeutic Chemical) code, or standard-specific codes for information used within the structured communication. The structured communication may include control characters or sequences of characters to indicate the beginnings, breaks, and/or ends of sections of the structured communication, for example, via a line end, a subsection break, tags enclosing sections or subsections, etc. One of ordinary skill in the art will be familiar with structured communications and their use, and additional details and uses thereof will not be provided herein, so as to not distract from the details of the present disclosure.

The pharmacy 110 receives prescription data, either directly from the patient (in the form of a paper prescription), or from a healthcare provider (in the form of an electronic prescription) and a confirmation from the patient to fill the prescription to begin the process of filling the prescription for the patient. In various aspects, at the time a patient provides a paper prescription or confirmation is given, the patient will also be queried for consent for patient-specific data to be applied to the determination of whether to apply a discount to the prescription. In other aspects, at the initial time a price is presented for a therapeutic that is eligible for a discount program, the patient may be queried for consent for patient-specific data to be applied to determine whether (additional) discounts are available for the therapeutic.

The pharmacy 110 transmits the prescription data to the clearinghouse 120, for example, via a structured communication according to an NCPDP standard. The clearinghouse 120 passes information about the therapeutic and the pharmacy 110 to the assistance analyzer 140 and transmits information about the patient's insurance coverage and the therapeutic to the PBM 130.

The assistance analyzer 140 will consult a database 150 with the information on the therapeutic and the pharmacy 110 to determine whether the therapeutic is eligible for an assistance program via the pharmacy 110. In aspects where the patient has given permission to use patient-specific information, the assistance analyzer 140 will query databases 160 for patient-specific information related to the demographics of the patient for comparison to the categories set by available assistance programs, to classify the patient as belonging to one or more categories.

In aspects where the patient has not yet given permission to use patient-specific information, the clearinghouse 120 will transmit a message to prompt the pharmacy 110 to ask the patient for permission to use patient-specific information. The message prompting for patient permission may include notices of category cutoffs to prompt the patients to supply permission by outlining categories of patients who are eligible for additional assistance via the program. For example, if persons making less that $X per year are eligible for assistance and persons making more than $X per year are not, the message may include a notice indicating the cutoff of $X. Similarly, if persons living in city X are eligible for assistance, a notice may indicate the geographic cutoff for eligibility. Categories include, but are not limited to: annual income, percentage of FPL, number of therapeutics prescribed, a geography of domicile or work (city, state, region, etc.), length of prescription, employment status, etc. In various aspects, the patient may give permission (or a refusal) via verbal, written, or automated forms, and the prescription (paper or electronic) may include the patient's grant of permission.

When the assistance analyzer 140 determines, based on the patient-specific data that it is permitted to access and the category definitions of the assistance program, that the patient belongs to a category of patients who are eligible for assistance, an assistance basis value is determined for the patient. The assistance basis value correlates to the out-of-pocket expense to a patient within the category that corresponds to a target adherence rate for the therapeutic. For example, for a target adherence rate of 75% for a given category, the assistance basis value is the out-of-pocket expense at which 75% of the patients belonging to the category are expected to adhere to the therapeutic. The assistance basis value for the patient may be selected from one category which the patient belongs to (e.g., the lowest, median, or highest assistance basis value, a preferred category) or may be a combination of assistance basis values (e.g., a mean (weighted or unweighted) assistance basis value).

The PBM 130 receives the information about the patient's insurance coverage and the therapeutic prescribed from the clearinghouse 120, and responds with a reimbursement schedule. The reimbursement schedule includes a copay amount for the patient to provide in order to receive the therapeutics, and may be formatted as a structured communication according to various standards (e.g., NCPDP). The assistance analyzer 140 compares the copay amount from the reimbursement schedule to an assistance basis for the patient to determine whether the copay amount exceeds the assistance basis, in which case additional assistance will be provided to lower the cost of the therapeutic to the assistance basis value, or as close as possible given a cap to assistance set by the assistance program.

The out-of-pocket expense is transmitted from the clearinghouse 120 to the pharmacy 110 as part of a structured document to charge the patient for the therapeutics. The out-of-pocket expense includes any reduction in price of the therapeutics due to insurance benefits and the assistance program, if available. Data on whether the patient fills the prescription (and is counted as adhering) or does not fill the prescription (and is counted as non-adhering) may be transmitted from the pharmacy 110 to the clearinghouse 120 so that adherence rates at given out-of-pocket expenses may be tracked and updated.

Figure 2:
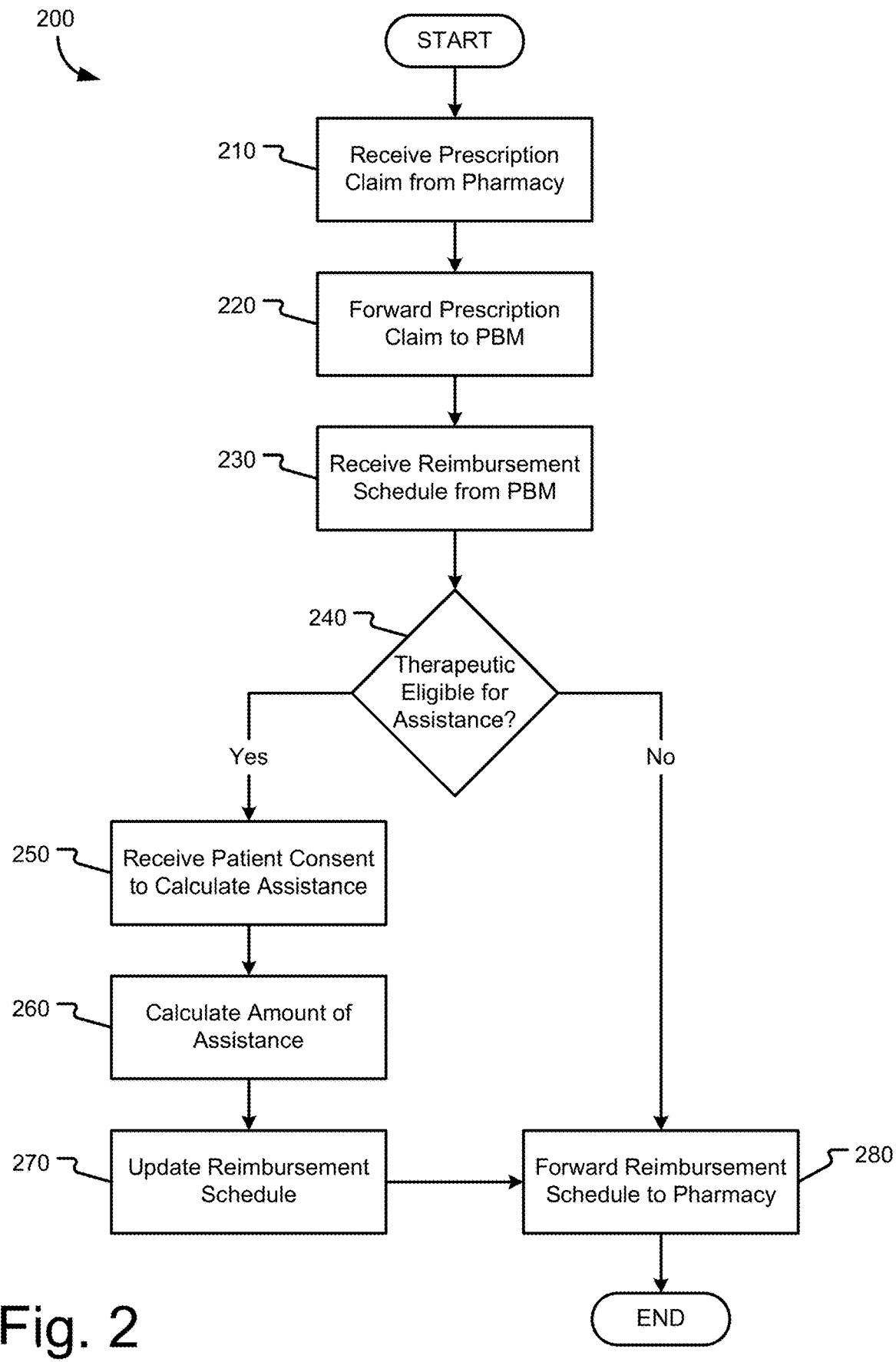
FIG. 2 is a flow chart showing general stages involved in an example method for providing patient assistance with patient-specific data in real-time.

FIG. 2 is a flow chart showing general stages involved in an example method 200 for providing patient assistance with patient-specific data in real-time. Method 200 begins at OPERATION 210, where a prescription claim is received from a pharmacy 110 at a clearinghouse 120. In various aspects, the prescription claim includes information about the patient, the therapeutic prescribed, and the PBM 130 with which the patient has a policy, and is formatted as a structured document (e.g., according to an NCPDP standard). In some aspects, when the patient provides a paper coupon, data from the paper coupon may be provided in the prescription claim, provided in a separate communication to the clearinghouse 120, or used locally by the pharmacy 110 at the time of payment after method 200 concludes.

Method 200 proceeds to OPERATION 220, where the prescription claim is forwarded, by the clearinghouse 120, to the PBM 130 indicated in the prescription claim. In various aspects, more than one PBM 130 may be forwarded the prescription claim, such as, for example, when the patient has multiple insurance policies. In various aspects when multiple PBMs 130 are contacted, the clearinghouse 120 may forward the prescription claim to all of the PBMs 130 at the same time (i.e., in parallel) or send the prescription claim to a first PBM 130 and wait to send the prescription claim to a subsequent PBM 130 (e.g., a supplemental insurance provider) until a response is received from the first PBM 130 at OPERATION 230 (i.e., in serial).

At OPERATION 230, the clearinghouse receives a reimbursement schedule from the contacted PBM 130, which either includes a copay amount for the patient to pay at the pharmacy 110 or an offset that the PBM 130 will apply to pay for the purchase of the therapeutic. The reimbursement schedule sets the amount which the patient will owe to the pharmacy 110 as a copay. For example, a first PBM 130, representing primary insurance, is contacted and returns a copay that will be the new basis for what the patient owes at the pharmacy, but a second PBM 130, representing secondary insurance, may be contacted to provide an additional offset for the patient's copay.

Method 200 proceeds to DECISION 240 to determine whether the therapeutic is eligible for assistance at the submitting pharmacy 110. Depending on the assistance program, various therapeutics may be eligible for assistance at various pharmacies 110. For example, a first pharmacy may participate in an assistance program for a first therapeutic, but not a second therapeutic, whereas a second pharmacy may participate in an assistance program for the second therapeutic, but not the first therapeutic. To determine whether a given therapeutic is eligible for assistance at the submitting pharmacy 110, the assistance analyzer compares the name (or code) of the pharmacy 110 and the name (or code) of the therapeutic from the prescription claim to entries in the database 150. In various aspects, the assistance analyzer 140 includes several matching circuits 302, discussed in greater detail regarding FIG. 3B, to determine whether names (or codes) match database entries. When the names (or codes) are determined to match entries in the database 150, method 200 proceeds to OPERATION 250. Otherwise, method 200 proceeds to OPERATION 280.

At OPERATION 250 patient consent to calculate assistance using patient-specific data is received. Patient consent data, in various aspects, are transmitted via a consent bit being flipped from zero/FALSE to one/TRUE in a structured communication, or as an encoding of a signature, a biometric marker, or other access control identifier. In some aspects, the pharmacy 110 may include patient consent data when submitting the prescription claim, leading into OPERATION 210. For example, the patient consent data may be included in the prescription claim or sent as a separate transmission. In other aspects, the pharmacy 110 may not send patient consent data (or may send data indicating lack of patient consent), and will be sent a transmission from the clearinghouse 120 when it is determined that the therapeutic is eligible for assistance at DECISION 240 to prompt the pharmacy 110 to query (or re-query) the patient for consent.

Method 200 proceeds from OPERATION 250 to OPERATION 260, where an amount of assistance is calculated, based on patient-specific data for which consent has been granted to access. In various aspects, the patient-specific data are held in a database 150 remote from the assistance analyzer 140, such as, for example, at a credit bureau, a bank, an employer of the patient, or a government agency. The assistance analyzer 140 will use the patient-specific data to determine what level of assistance should be provided to the patient. The patient-specific data, which may include demographic data (e.g., age, race, gender), a geographic location of the patient (e.g., an address, city, region, or state of domicile, birth, or work), a credit score, a percentage of the Federal Poverty Level (FPL), an employment status, etc., are matched to various categories and compared against adherence rates to determine how to best encourage the patient to adhere to treatment.

In various aspects, to assist the patient to adhere to a course of treatment based on the patient-specific data, the assistance analyzer 140 will aggregate prescription data, cost data, adherence data, and patient-specific data from several patients to create adherence rates that are applicable to specific patient-bases that share a feature (or features) in common (e.g., living in city X, having gender Y, living in city X and having gender Y). For example, it may be determined that for patients in city X charged $50 for a given class of therapeutics an adherence rate is 75%, but when those same patients are charged $60, the adherence rate is 70% and when those same patients are charged $40, the adherence rate is 80%. Similarly, it may be determined that for patients in city Y charged $50 for a given class of therapeutics an adherence rate is 60%, but when those same patients are charged $60, the adherence rate is 45% and when those same patients are charged $40, the adherence rate is 75%. Adherence rates are updated as particular patients within those categories adhere or fail to adhere to their treatments.

The assistance analyzer 140 is further operable to interpolate adherence rates for price points between collected data points and extrapolate adherence rates for price points beyond collected data points. For example, if adherence rates for the out-of-pocket costs of $40, $50, and $60 have been collected, adherence rates for any value between $40 and $60 may be calculated via interpolation, for example, via linear, polynomial, spline, or Gaussian interpolation. Similarly, for example, if adherence rates for the out-of-pocket costs of $40, $50, and $60 have been collected, adherence rates for values price points above $60 or below $40 may be extrapolated, for example, via linear, polynomial, conic, Richardson, or French curve extrapolation. As will be appreciated, data for other categories may be used when interpolating or extrapolating to increase the accuracy of the estimates. For example, if data exist for adherence rates in category Y (e.g., city of domicile Y, therapeutic Y, income bracket Y, etc.) for a given out-of-pocket expense, but not for category X (e.g., city of domicile X, therapeutic X, income bracket X, etc.), the data or data trends from category Y may be adjusted for application to category X when extrapolating or interpolation data relative to category X.

Depending on a threshold for an adherence rate, the assistance analyzer 140 will determine an amount of assistance to apply to meet a threshold of adherence. As will be appreciated, an adherence rate of 100% for a given therapeutic is likely impossible to achieve, because patients may avoid filling prescriptions for a variety of reasons, including, but not limited to: side effects, out-of-pocket cost, disagreement regarding a need for the therapeutic, and forgetfulness. Therefore, a target adherence rate may be set by a manufacturer for an adherence rate less than 100% to match the desired practical adherence rate for a patient-base.

As part of OPERATION 260, the assistance analyzer 140 will determine various categories to which the patient belongs, based on the patient-specific data, and correlate the adherence rates for various out-of-pocket expenses to the patient's categories at the target adherence rate. A patient may be determined to belong to several categories, such as, for example, patients in the Nashville metropolitan area, patients in the $25,000 to $35,000 annual earning bracket, patients in the 110-120% of FPL bracket, patients prescribed n therapeutics, etc. Each of these categories may have different adherence rates at different price points, and the assistance analyzer 140 will use the target adherence rate to find the out-of-pocket expense for each of the categories. For example, for a target adherence rate of 70%, patients in the Nashville metropolitan area may have a 70% adherence rate at an out-of-pocket expense of $50, patients in the $25,000 to $35,000 annual earning bracket at an out-of-pocket expense of $45, patients in the 110-120% of FPL bracket at an out-of-pocket expense of $30, patients prescribed n therapeutics an out-of-pocket expense of $60, etc. In various aspects, the assistance analyzer 140 will use one of the out-of-pocket expense values as an assistance basis value (e.g., from a preferred category, the highest value, the lowest value, the median value), while in other aspects, the assistance analyzer 140 will use an average of the values as the assistance basis value. When using an average, the out-of-pocket expense values may be weighted (by category preference, to eliminate outliers, etc.) or be taken as a straight average (mean) of the values.

The assistance analyzer 140 uses the assistance basis value as a target that the patient's out-of-pocket expense is to be reduced to. In various aspects, the assistance analyzer 140 will apply any coupons (electronic or paper) to the patient's out-of-pocket expense to apply assistance until the assistance basis value is reached. For example, with an assistance basis value of $50, and a patient whose insurance sets a copay of $45, no assistance will be applied, whereas for a patient whose insurance sets a copay of $60, assistance equivalent to $10 will be applied to reach the assistance basis value. In aspects where the rules of an assistance program set an assistance cap, and the amount of assistance needed to reach the assistance basis value exceeds the cap, the maximum value of assistance (i.e., the assistance cap) will be offered, and the manufacturer will be contacted (e.g., via an email or summary report) to alert the manufacturer to make an exception to the cap or for record keeping purposes.

At OPERATION 270, the reimbursement schedule is updated to reflect any offsets or assistance available to the patient. In various aspects, the assistance analyzer uses subtractor circuits 303, as discussed in regard to FIG. 3C, to subtract offsets from the PBM 130 and any available coupon amounts from the initial cost. In aspects where the PBM 130 returns a copay, rather than an offset, in the reimbursement schedule, the coupon amounts will be subtracted from the copay in the reimbursement schedule. In aspects where multiple PBMs 130 were contacted in OPERATION 220, the copay/offset that each offers from an original cost of the therapeutics in the prescription claim will be applied either additively or the best (e.g., the largest or associated with a specified deductible) will be selected to be applied to the initial amount.

Method 200 then proceeds to OPERATION 280, where the updated reimbursement policy is forwarded to the pharmacy 110 for the patient to pay the stated amount. Method 200 then concludes.

FIGS. 3A-E illustrate various circuit diagrams for circuits applicable to digital devices, such as an assistance analyzer 140, operable to perform various rules and comparisons as part of the systems and devices of the present disclosure. As illustrated in FIGS. 3A-E, bits from a first data source are labeled with an "a" and bits from a second data source are labeled with a "b" so that their source may be readily apparent. First input bits 311 and nth input bits 312 correspond to different bits on which data are encoded, comprising the data from the first and second data sources being compared, such that first input bit 311*a* and nth input bit 312*a* are from the first data source, and first input bit 311*b* and nth input bit 312*b* are from the second data source.

The circuits are sized to accommodate the largest possible data field from the clearinghouse 120. For example, when a data field contains a maximum of twelve characters, each character being encoded in one byte (e.g., according to ASCII or a basic Latin set from the UTF-8 standard), the logic gate array will accept up to 192 inputs (i.e., 12*8*2 inputs). When the data within a data field do not fully fill that data field, such as when only twelve characters are encoded in a field with a maximum size of thirteen characters, any unused bits may be set to zero/FALSE or no input to the corresponding leads of a given logic gate array will provided.

An arrayed logic gate will accept multiple inputs to produce a single output per the truth table of the logic gate. For example, an AND logic gate array 320 will accept n inputs and produce one output, wherein than one output will return zero/FALSE unless all of the n inputs are one/TRUE, in which case it will return one/TRUE. In another example, an OR logic gate array 330 will accept n inputs and will produce one output, wherein that one output will return one/TRUE if any of then inputs is one/TRUE, otherwise the logic gate array will return zero/FALSE. One of ordinary skill in the art will be familiar with the truth tables of different logic gate arrays. One of ordinary skill in the art will also be familiar with the construction of logic gate arrays from various transistors (e.g., Bipolar Junction (BJT), Field Effect (FET), etc.), diodes, resistors, memristors, and combinations thereof that are stand-alone electrical components, part of an integrated circuit, or provided by a processor.

As will be appreciated, a rule may make multiple uses of one or more of the example circuits to provide greater nuance in comparisons between data sources. For example, multiple existence checks may be performed against a rule definition to determine whether an input falls outside of a range (or falls within a category of a plurality of categories). The multiple outputs from these circuits may be combined via AND or OR operations to return a passing state or a failing state of the rule. Alternatively, when only one circuit is used, its output's state may be used to return a passing or failing state of the rule.

Figure 3A:
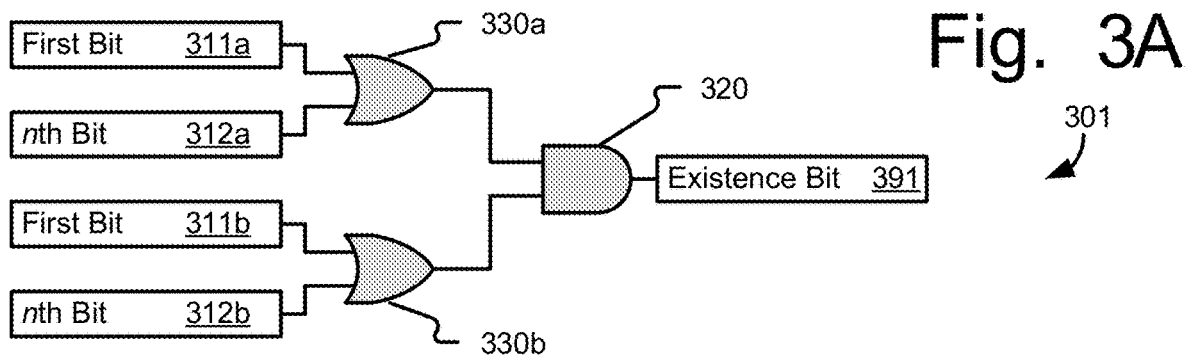
FIGS. 3A-E illustrate various circuit diagrams for circuits operable to perform functions provided by an assistance analyzer.

FIG. 3A is an example diagram of an existence circuit 301 corresponding to a rule for comparing whether data coexist in data inputs. As illustrated, each of the bits from two data sources are input into an OR logic gate array 330. First input bit 311*a* through nth input bit 312*a* from the first data source are fed into a first OR logic gate array 330*a*, and first input bit 311*b* through nth input bit 312*b* from the second data source are fed into a second OR logic gate array 330*b*. The output of the first OR logic gate array 330*a* is then combined with the output of the second OR logic gate array 330*b* via an AND logic gate array 320 to produce an existence bit 391 to indicate that the data from the first and second data sources exist, as defined by each other, with a one/TRUE value, or that at least one does not exist with a zero/FALSE value. As will be appreciated, if the first data source represents a rule definition that is known to exist, the first OR logic gate array 330*a* may be replaced with a one/TRUE value input to reduce the number of logic gate arrays required.

Figure 3B:
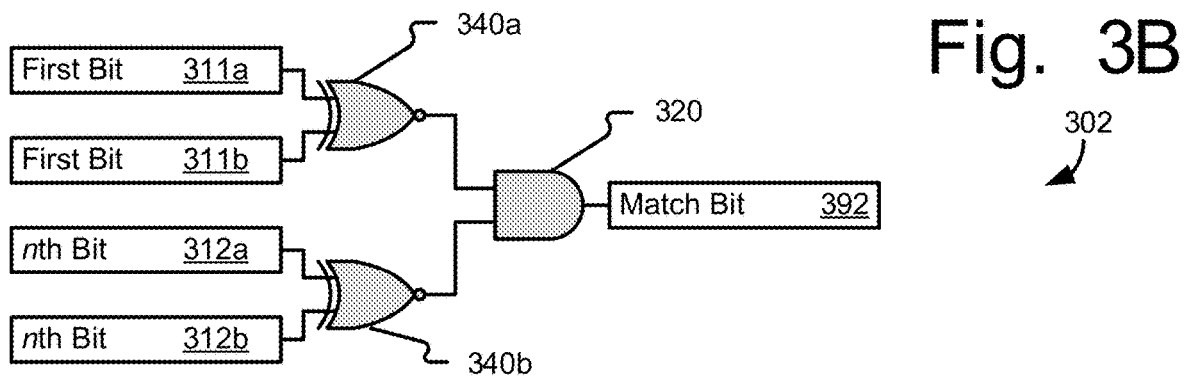

FIG. 3B is an example diagram for a matching circuit 302 corresponding to a rule for comparing whether the data from the first and second data sources match. Each bit from the first data source is combined with the corresponding bit from the second data source via an XNOR logic gate array 340. For example, a first input bit 311*a* from a rule definition will be XNORed with a first input bit 311*b* from a data source via a first XNOR logic gate array 340*a*, and an nth input bit 312*a* from a rule definition will be XNORed with an nth input bit 312*b* from the data source via an nth XNOR logic gate array 340*b*. The output of the first XNOR logic gate array 340*a* is then combined with the output of the nth XNOR logic gate array 340*b* via an AND logic gate array 320 to produce a match bit 392 to indicate a match with a one/TRUE value, or no match with a zero/FALSE value.

A rule may allow for inexact matches as well as exact matches. Therefore, the input bits to the matching circuit 302 may be substituted or discarded from consideration via bit shifting or ignoring portions of the data to be compared. For example, input data for a personal name may be "DOE JOHN", whereas a rule definition for a name may have "DOE JOHN Q", and the bits used to encode the extra "Q", which are not found in the input data, may be ignored so that the data may be considered to be matching. Similarly, if a different rule definition used the name value "DOE JONATHAN", the term "JONATHAN" could be recognized by a separate matching circuit 302 so that the term "JOHN" may be substituted for "JONATHAN" when comparing the data, so that an inexact match will return one/TRUE. In various aspects, the separate circuits for exact and inexact matches may be combined via an OR gate to provide a single output.

Figure 3C:
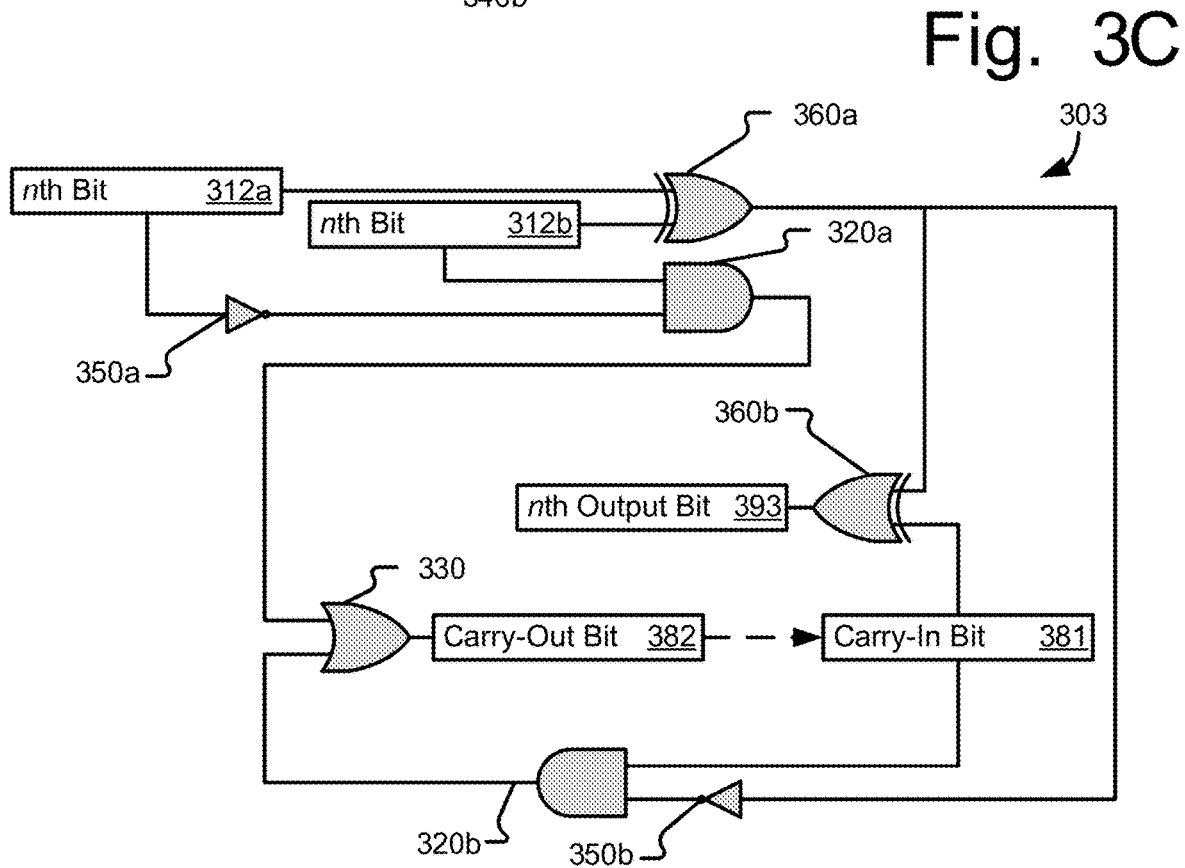

FIG. 3C is an example diagram for a bitwise subtractor circuit 303 corresponding to a rule for finding the difference between two sets of data. In various aspects, before subtracting one set of data from another, the values of those data are converted from character representations of digits of that number (e.g., in the UTF-8 or ASCII formats) to a binary representation of that number. For example, the number twelve in UTF-8 format is represented as two characters (i.e., "1" and "2"), each with its own encoding for the digit it represents ($0011\ 0001_{x2}$ and $0011\ 0010_{x2}$, respectively), whereas the number twelve in binary notation is represented as $0000\ 1100_{x2}$. As will be understood, there are multiple ways to represent a number in a binary format that account for negative and fractional numbers, and the precise format may vary in different aspects so long as the number is represented as a whole and not via individual representations of the digits.

As will be recognized, bitwise subtraction operations include inputs bits for a minuend, a subtrahend, and a carry-in, and produce outputs bits for a difference and a carry-out. The minuend is the input from which the subtrahend is subtracted, which are illustrated as the nth input bit 312a from the first data source and the nth input bit 312b from the second data source respectively.

A carry-in bit 381 represents "carry-over" from a previous bitwise subtraction operation (e.g., from the (n−1)th bits from the two data sources) and a carry-out bit 382 represents "carry-over" from the current operation to the next bitwise subtraction operation (e.g., for the (n+1)th bits from the two data sources). The carry-in bit 381 for the first bits subtracted will be zero/FALSE, but for any subsequent bits will be equal to the carry-out bit 382 from the previous bits' operation. Thus, for subtraction of numbers represented n bits, n or more bitwise subtractor circuits 303 are chained together by their carry-in bits 381 and carry-out bits 382, and the chain begins with the least significant bits representing the two numbers.

In the example diagram, the value of the carry-out bit 382 is determined via an OR logic gate array 330, which takes its inputs from the outputs of a first AND logic gate array 320a and a second AND logic gate array 320b. The first AND logic gate array 320a uses the subtrahend and an inversion of the minuend's value, via first inverter 350a, as inputs for an AND operation. The second AND logic gate array 320b uses the carry-in bit 381 and an inversion, via second inverter 350b, of a XORing, via first XOR logic gate array 360a, of the minuend and the subtrahend as inputs for an AND operation.

In the example diagram, the minuend is XORed with the subtrahend via the first XOR logic gate array 360a, which is in turn XORed with the carry-in bit 381 via the second XOR logic gate array 360b to produce the nth output bit 393. The carry-in bit 381 is equal to the carry-out bit 382 for the previous subtraction operation. Each operation of the bitwise subtractor circuit 303 results in one output bit 393, and the output bits 393 are assembled into the difference between the numbers from the two structured sets of data in order from least significant bit to most significant bit. For example, for the operation of four ($0100_{x2}$) minus two ($0010_{x2}$), the first output bit 393 would be zero/FALSE and the second output bit 393 would be one/TRUE to yield the difference of two ($0010_{x2}$) with zero/FALSE in the least significant position and one/TRUE in the next most significant position based on the order of output from the example bitwise subtractor circuit 303.

In various aspects, a series of subtractor circuits 303 are used in combination with an existence circuit 301 to determine whether a value exceeds the bounds of a threshold rule. For example, for determining whether a value is greater than a threshold, a series of subtractor circuits 303 will be used subtract a threshold from a value, and the result is checked via an existence circuit 301 to see if the result has a positive value, indicating that the value is greater than the threshold. In an alternative example, for determining whether a value is less than a threshold, series of subtractor circuits 303 will be used to subtract the value from the threshold, and the result is checked via an existence circuit 301 to see if the result has a positive value, indicating that the value is less than the threshold. As will be appreciated, depending on how negative and positive values are tracked, a bit used to indicate sign (i.e., positive or negative), may be ignored by the existence circuit 301 in the above examples.

Figure 3D:
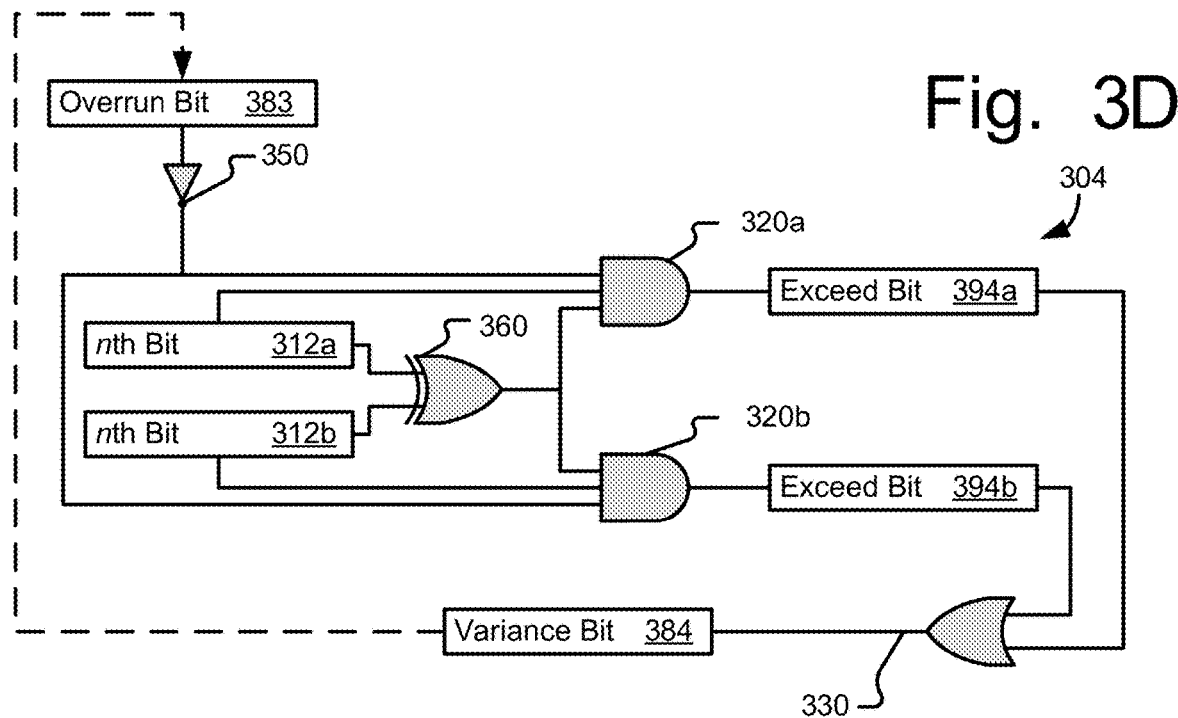

FIG. 3D is an example diagram for a bitwise sizing circuit 304 corresponding to a rule for finding which of two sets of data has the greater (or lesser) value. A sizing circuit 304 may be used to determine whether input from a first data source exceeds input from a second data source. Similarly to a subtractor circuit 303, the values of these data are converted from character representations of digits of a number to a binary representation of that number as a whole before inputting those data to the sizing circuit 304. As will be understood, there are multiple ways to represent a number in a binary format that account for negative and fractional numbers, and the precise format may vary in different aspects so long as the number is represented as a whole and not via individual representations of the digits.

As will be recognized, bitwise sizing operations include inputs bits from the data sources to compare and an overrun, and produce outputs bits for indicating whether one set of data is greater than the other and a variance. The inputs from the data sources are illustrated as the nth input bit 312a from the first data source and the nth input bit 312b from the second data source respectively.

An overrun bit 383 represents "carry-over" from a previous bitwise sizing operation (e.g., from the (n+1)th bits from the two data sources) and a variance bit 384 represents "carry-over" from the current operation to the next bitwise sizing operation (e.g., to the (n−1)th bits from the two data sources). The overrun bit 383 for the first bits sized will be zero/FALSE, but for any subsequent bits will be equal to the variance bit 384 from the previous bits' operation. Thus, for sizing numbers represented n bits, n or more bitwise sizing circuits 304 are chained together by their overrun bits 383 and variance bits 384, and the chain begins with the most significant bits representing the two numbers. As will be appreciated, if a given number includes fewer bits in its representation than another number, it will be padded with leading zeroes so that the comparison of most significant bits will compare the same values, accounting for any bits used for designating negative/positive values (e.g., when comparing binary five ($0101_{x2}$) to binary twenty-five ($0001\ 1001_{x2}$), binary five may be padded to be represented as $0000\ 0101_{x2}$ for a bitwise comparison with twenty-five).

In the example diagram, each exceed bit 394 represents whether the associated nth input bit 312 is larger than the nth input bit 312 from the other data source. For example, first exceed bit 394a will be one/TRUE when first nth input bit 312a (associated with the first data source) exceeds second nth input bit 312b (associated with the second data source). Similarly, second exceed bit 394b will be one/TRUE when second nth input bit 312b exceeds first nth input bit 312a. A given bit exceeds another bit when the given bit is equal to one/TRUE and the other bit is equal to zero/FALSE.

Starting with the most significant bits, nth input bit 312a is compared with nth input bit 312b via an XOR logic gate array 360, the result of which is input to first AND logic gate array 320a and second AND logic gate array 320b. Each of the AND logic gate arrays 320 also accept an inversion of the overrun bit 383, produced by inverter 350, and the associated nth input bit 312 as inputs. First AND logic gate array 320a produces exceed bit 394a to indicate that nth input bit 312a exceeds nth input bit 312b, and that no data source in a previous iteration was determined to exceed the other by setting exceed bit 394a to one/TRUE, and otherwise setting it to zero/FALSE. Second AND logic gate array 320b produces exceed bit 394b to indicate that nth input bit 312b exceeds nth input bit 312a, and that no data source in a previous iteration was determined to exceed the other by setting exceed bit 394b to one/TRUE, and otherwise setting it to zero/FALSE.

To ensure that the sizing circuit 304 tracks whether bits of greater significance from the data sources have already determined that one dataset is greater than the other, the first exceed bit 394a and the second exceed bit 394b are combined via an OR logic gate array 330 to produce the variance bit 384. The value of the variance bit 384 is used as the value for the overrun bit 383 for the next-most significant bit to be compared by the sizing circuits 304 in the series.

When the data from the first and second data sources are equal, the exceed bits 394a, 394b will all produce zero/FALSE, but when the data from one data source exceeds the other's data (i.e., has a higher value), the associated exceed bit 394 from the first iteration of the chain of sizing circuits 304 that determines that one set of data exceeds the other will produce one/TRUE and all other exceed bits 394 will produce zero/FALSE. As will be appreciated, each of the first exceed bits 394a and second exceed bits 394b may be aggregated and combined via associated aggregating OR logic gate arrays 330 (not illustrated; one for all the first exceed bits 394a and one for all the second exceed bits 394b) between each iteration of the sizing circuit 304 for a single determination to be provided. Alternatively, each iteration of the sizing circuit 304 in a chain of sizing circuits 304 may write to the same bit, if the variance bit 384 enables a breakout from the series of circuits, in which case the overrun bit 383, inverter 350, and supporting circuitry may be omitted.

Figure 3E:
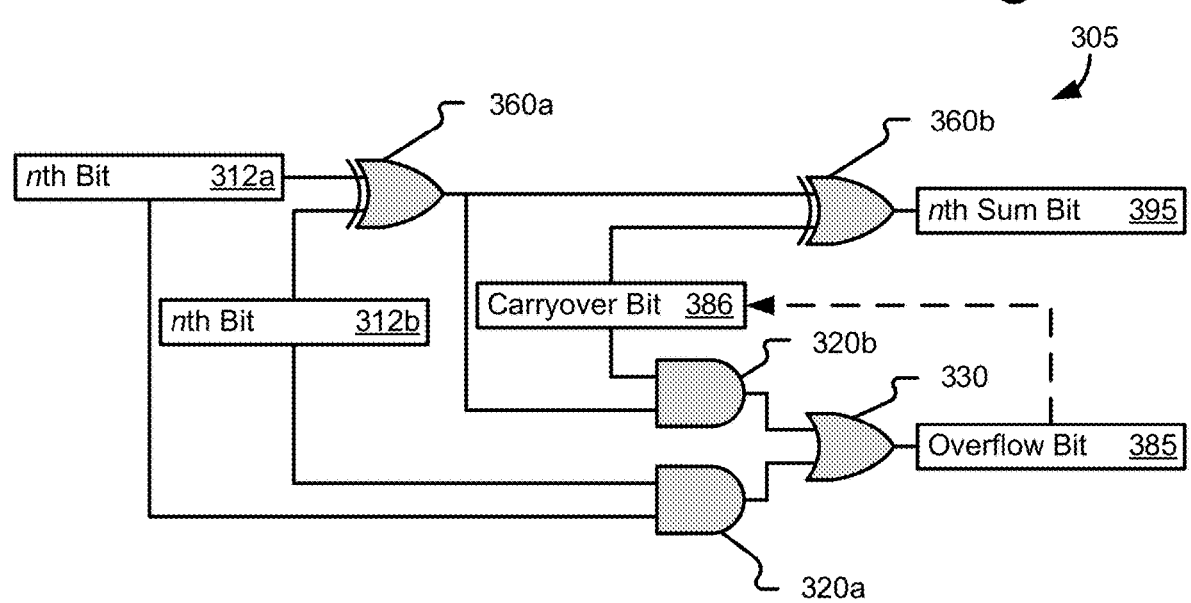

FIG. 3E is an example diagram for a bitwise full-adder circuit 305 corresponding to a rule for finding the sum of two sets of data. Similarly to subtractor circuits 303 and sizing circuits 304, the values of these data are converted from character representations of digits of a number to a binary representation of that number as a whole before inputting those data to the full-adder circuit 305. As will be understood, there are multiple ways to represent a number in a binary format that account for negative and fractional numbers, and the precise format may vary in different aspects so long as the number is represented as a whole and not via individual representations of the digits.

As will be recognized, bitwise addition operations include inputs bits for the terms to be added and a carryover, and produce outputs bits for a sum and an overflow. The terms are the bits from the data sources, which are illustrated as the nth input bit 312a from the first data source and the nth input bit 312b from the second data source respectively.

A carryover bit 386 represents "carry-over" from a previous bitwise addition operation (e.g., from the (n−1)th bits from the two data sources) and an overflow bit 385 represents "carry-over" from the current operation to the next bitwise addition operation (e.g., for the (n+1)th bits from the two data sources). The carryover bit 386 for the first bits added will be zero/FALSE, but for any subsequent bits will be equal to the overflow bit 385 from the previous bits' operation. Thus, for addition of numbers represented n bits, n or more bitwise full-adder circuits 305 are chained together by their carryover bits 386 and overflow bits 385, and the chain begins with the least significant bits representing the two numbers, which is referred to as a ripple full-adder.

As illustrated, nth sum bit 395 is the product of an XOR operation at second XOR logic gate array 360b of the carryover bit 386 and the product of the first XOR logic gate array 360a of the nth input bit 312a and the nth input bit 312b. To produce the overflow bit 385, which is used as the carryover bit 386 for a subsequent full-adder circuit 305 in a ripple full-adder, the output of the first AND logic gate array 320a and the output of the second AND gate array 320b are ORed by OR logic gate array 330. The first AND logic gate array 320a uses the carryover bit 386 and the output of the first XOR logic gate array 360a as inputs, and the second AND logic gate array 320b uses the nth input bit 312a and the nth input bit 312b as inputs. For example, for the operation of one ($0001_{x2}$) plus three ($0011_{x2}$), the first sum bit 395 would be zero/FALSE (with an first overflow bit 385 of one/TRUE), the second sum bit 395 would be zero/FALSE (with an first overflow bit 385 of one/TRUE), the third sum bit 395 would be one/TRUE (with an first overflow bit 385 of zero/FALSE), to yield the sum of four ($0100_{x2}$) with zero/FALSE in the two least significant positions and one/TRUE in the second most significant position based on the order of output from the example bitwise full-adder circuit 305.

As will be understood, several rule circuits may be chained together, and the example rule circuits given herein are non-limiting examples of potential rules circuits that may be used to affect rules.

For example, a first matching circuit 302 may be combined with a second matching circuit 302 as a matcher chain to determine whether an assistance program exists for a therapeutic and whether the pharmacy 110 is participating in the assistance program. In some aspects, the two matching circuits 302 chains run in series, where the match bit 392 from the first matching circuit 302 is used to determine whether to run the second matching circuit 302, while in other aspects, the two matching circuits 302 are run in parallel. As will be appreciated, when the matcher chain is run in series, the first matching circuit 302 is used to compare bitwise data from a first matching source (e.g., for a therapeutic from a prescription) to bitwise data from a second matching source (e.g., a database 150 on which therapeutics have assistance programs) and the second matching circuit 302 is used for comparing bitwise data from a third matching source (e.g., having data identifying the submitting pharmacy 110 of a prescription) to bitwise data from a fourth matching source (e.g., data from a database 150 on which pharmacies are participating in the therapeutic's assistance programs). Which matching circuit 302 is run first in a serial matcher chain may vary, depending on which dataset (therapeutics or pharmacies) held by the database 150 for identifying available assistance programs contains more entries or is more reliable (with the smaller or more reliable being compared by the first matching circuit 302). The match bit 392 of the second matching circuit 302, when the matcher chain is run in series, may then be used to determine whether to attempt to apply assistance to the patient's out-of-pocket costs. Similarly, when the matcher chain is run in parallel, a combined match bit 392 of the two match bits 392 from the first and second matching circuits 302 (combined via an AND logic gate array 320), may then be used to determine whether to attempt to apply assistance to the patient's out-of-pocket costs.

In another example, when attempting to apply assistance to the patient's out-of-pocket costs, a chain of sizing circuits 304 is used to determine whether the initial out-of-pocket cost received from the PBM 130 is greater than or less than a targeted out-of-pocket cost of the available assistance program (e.g., the assistance basis). When an exceed bit 394 associated with the initial out-of-pocket cost being greater is one/TRUE, the exceed chain will signal that assistance is to be applied, and the patient's reimbursement schedule is to be updated to reflect the assistance. Otherwise, when no exceed bit 394 is one/TRUE or the exceed bit 394 associated with the initial out-of-pocket cost being lesser is one/TRUE, the reimbursement schedule may be left unadjusted.

In a further example, when the patient's reimbursement schedule is to be updated, a chain of subtractor circuits 303 and sizing circuits 304 is used to determine how much assistance to apply to reduce the patient's out-of-pocket costs. Subtractor circuits 303 are chained together to determine a difference between the assistance basis and the initial out-of-pocket expense, which in turn is checked against an assistance cap for the assistance program, stored by a database 150, via a chain of sizing circuits 304. When the difference is less than the cap, as indicated by an associated exceed bit 394, the reimbursement schedule is adjusted to request the assistance basis from the patient as the out-of-pocket expense. When the difference is greater than the cap, as indicated by a different associated exceed bit 394, the reimbursement schedule is adjusted to request the cap from the patient as the out-of-pocket expense. In various aspects, the exceed bits 394 may be used to control a gate or switch, so that the register containing the initial out-of-pocket expense from the PBM 130 will always be replaced, but which data replace the initial out-of-pocket expense will be determined by the state of the exceed bits 394.

Figure 4:
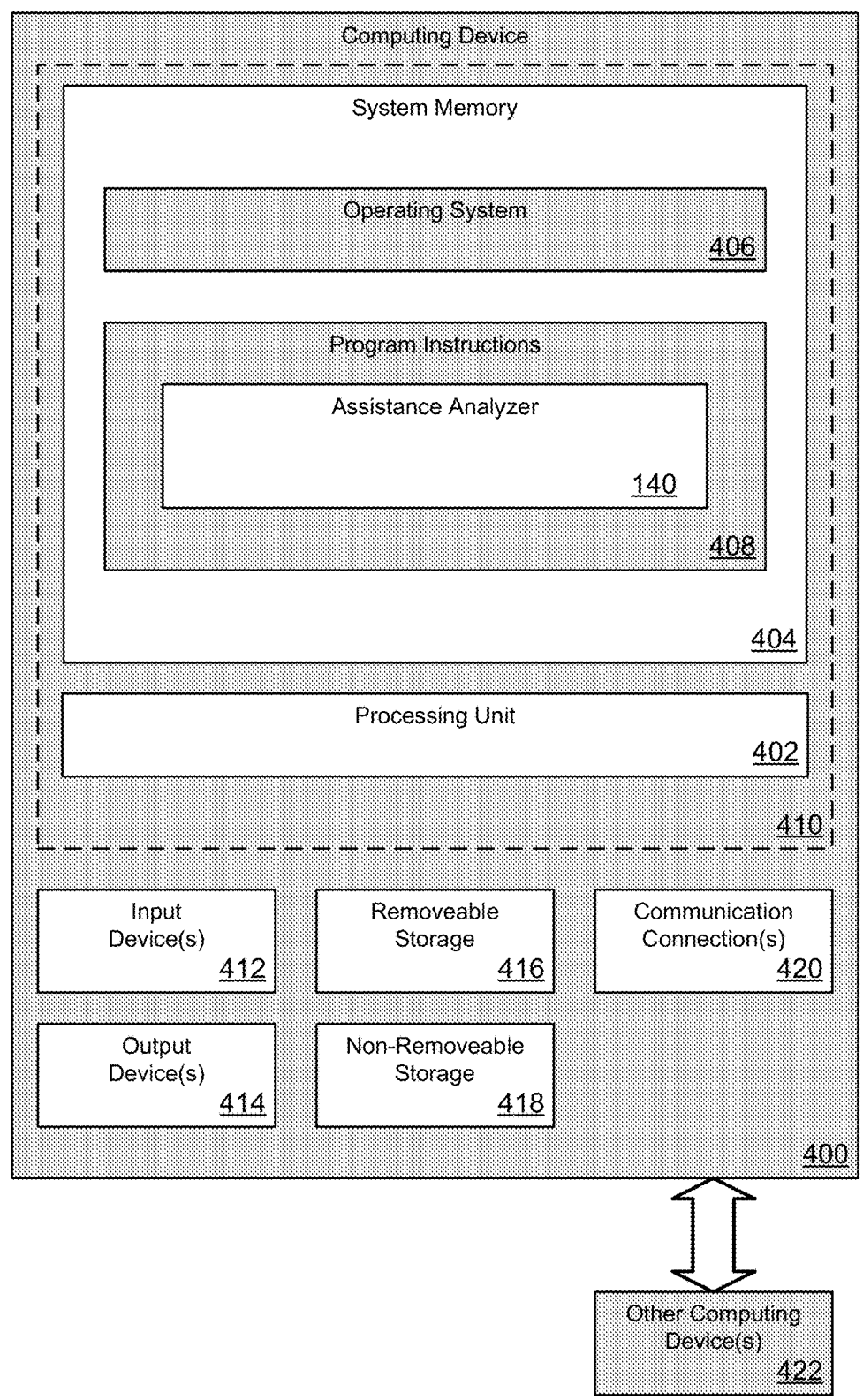
FIG. 4 is a block diagram illustrating physical components of an example computing device with which aspects may be practiced.

FIG. 4 is a block diagram illustrating physical components of an example computing device with which aspects may be practiced. The computing device 400 may include at least one processing unit 402 and a system memory 404. The system memory 404 may comprise, but is not limited to, volatile (e.g. random access memory (RAM)), non-volatile (e.g. read-only memory (ROM)), flash memory, or any combination thereof. System memory 404 may include operating system 406, one or more program instructions 408, and may include sufficient computer-executable instructions for an assistance analyzer 140, which when executed, perform functionalities as described herein. Operating system 406, for example, may be suitable for controlling the operation of computing device 400. Furthermore, aspects may be practiced in conjunction with a graphics library, other operating systems, or any other application program and is not limited to any particular application or system. This basic configuration is illustrated by those components within a dashed line 410. Computing device 400 may also include one or more input device(s) 412 (keyboard, mouse, pen, touch input device, etc.) and one or more output device(s) 414 (e.g., display, speakers, a printer, etc.).

The computing device 400 may also include additional data storage devices (removable or non-removable) such as, for example, magnetic disks, optical disks, or tape. Such additional storage is illustrated by a removable storage 416 and a non-removable storage 418. Computing device 400 may also contain a communication connection 420 that may allow computing device 400 to communicate with other computing devices 422, such as over a network in a distributed computing environment, for example, an intranet or the Internet. Communication connection 420 is one example of a communication medium, via which computer-readable transmission media (i.e., signals) may be propagated.

Programming modules, may include routines, programs, components, data structures, and other types of structures that may perform particular tasks or that may implement particular abstract data types. Moreover, aspects may be practiced with other computer system configurations, including hand-held devices, multiprocessor systems, microprocessor-based or programmable user electronics, minicomputers, mainframe computers, and the like. Aspects may also be practiced in distributed computing environments where tasks are performed by remote processing devices that are linked through a communications network. In a distributed computing environment, programming modules may be located in both local and remote memory storage devices.

Furthermore, aspects may be practiced in an electrical circuit comprising discrete electronic elements, packaged or integrated electronic chips containing logic gates, a circuit using a microprocessor, or on a single chip containing electronic elements or microprocessors (e.g., a system-on-a-chip (SoC)). Aspects may also be practiced using other technologies capable of performing logical operations such as, for example, AND, OR, and NOT, including, but not limited to, mechanical, optical, fluidic, and quantum technologies. In addition, aspects may be practiced within a general purpose computer or in any other circuits or systems.

Aspects may be implemented as a computer process (method), a computing system, or as an article of manufacture, such as a computer program product or computer-readable storage medium. The computer program product may be a computer storage medium readable by a computer system and encoding a computer program of instructions for executing a computer process. Accordingly, hardware or software (including firmware, resident software, microcode, etc.) may provide aspects discussed herein. Aspects may take the form of a computer program product on a computer-usable or computer-readable storage medium having computer-usable or computer-readable program code embodied in the medium for use by, or in connection with, an instruction execution system.

Although aspects have been described as being associated with data stored in memory and other storage mediums, data can also be stored on or read from other types of computer-readable media, such as secondary storage devices, like hard disks, floppy disks, or a CD-ROM, or other forms of RAM or ROM. The term computer-readable storage medium refers only to devices and articles of manufacture that store data or computer-executable instructions readable by a computing device. The term computer-readable storage media do not include computer-readable transmission media.

Aspects of the present invention may be used in various distributed computing environments where tasks are performed by remote processing devices that are linked through a communications network.

Aspects of the invention may be implemented via local and remote computing and data storage systems. Such memory storage and processing units may be implemented in a computing device. Any suitable combination of hardware, software, or firmware may be used to implement the memory storage and processing unit. For example, the memory storage and processing unit may be implemented with computing device 400 or any other computing devices 422, in combination with computing device 400, wherein functionality may be brought together over a network in a distributed computing environment, for example, an intranet or the Internet, to perform the functions as described herein. The systems, devices, and processors described herein are provided as examples; however, other systems, devices, and processors may comprise the aforementioned memory storage and processing unit, consistent with the described aspects.

The description and illustration of one or more aspects provided in this application are intended to provide a thorough and complete disclosure the full scope of the subject matter to those skilled in the art and are not intended to limit or restrict the scope of the invention as claimed in any way. The aspects, examples, and details provided in this application are considered sufficient to convey possession and enable those skilled in the art to practice the best mode of the claimed invention. Descriptions of structures, resources, operations, and acts considered well-known to those skilled in the art may be brief or omitted to avoid obscuring lesser known or unique aspects of the subject matter of this application. The claimed invention should not be construed as being limited to any embodiment, aspects, example, or detail provided in this application unless expressly stated herein. Regardless of whether shown or described collectively or separately, the various features (both structural and methodological) are intended to be selectively included or omitted to produce an embodiment with a particular set of features. Further, any or all of the functions and acts shown or described may be performed in any order or concurrently. Having been provided with the description and illustration of the present application, one skilled in the art may envision variations, modifications, and alternate embodiments falling within the spirit of the broader aspects of the general inventive concept provided in this application that do not depart from the broader scope of the present disclosure.

I claim:

1. A method for improving functionality of systems for patient access to prescribed therapeutics, comprising:
   receiving a prescription claim from a pharmacy, wherein the prescription claim identifies a patient and a therapeutic;
   forwarding the prescription claim to a prescription benefit manager (PBM);
   receiving a reimbursement schedule from the PBM, wherein the reimbursement schedule sets forth a copayment amount owed by the patient for the therapeutic;
   determining whether the therapeutic is eligible for adherence assistance at the pharmacy;
   when it is determined that the therapeutic is eligible for adherence assistance, calculating an amount of assistance; and
   updating the reimbursement schedule to reflect the amount of assistance available to the patient; and
   forwarding the updated reimbursement schedule to a computing device associated with the pharmacy.

2. The method of claim 1, wherein the prescription claim received from the pharmacy includes a patient consent to use personal data.

3. The method of claim 1, wherein the prescription claim received from the pharmacy does not include a patient consent to use personal data, further comprising:
   transmitting a consent request to the pharmacy to transmit the patient consent to use the personal data when it is determined that the therapeutic is eligible for adherence assistance;
   when the patient consent to use the personal data is received, calculating the amount of assistance based on the personal data; and
   when the patient consent to use the personal data is not received, calculating the amount of assistance based on aggregated data.

4. The method of claim 3, wherein the personal data are used to determine a percentage of Federal Poverty Level for the patient.

5. The method of claim 3, wherein the personal data include a credit score provided by a credit bureau.

6. The method of claim 3, wherein the personal data include geography data for the patient.

7. A system having improved functionality for improving patient access to prescribed therapeutics, comprising:
   a clearinghouse computing device to receive a prescription claim associated with a patient from a pharmacy computing device;
   a Pharmacy Benefits Manager computing device, operable to receive the prescription claim from the clearinghouse computing device and, in response, transmit a reimbursement schedule to the clearinghouse computing device, wherein the reimbursement schedule includes a copayment amount for the prescribed therapeutic based on an insurance policy of the patient; and
   a database, including patient-specific data, in communication with the clearinghouse computing device;
   wherein the prescription claim and the reimbursement schedule are structured communications;
   wherein the clearinghouse computing device includes an assistance analyzer, operable to compare the patient-specific data with the structured communications to determine whether the patient is eligible to receive personalized assistance for adhering to the prescribed therapeutics;
   wherein the assistance analyzer determines an amount of the personalized assistance based on historic adherence rates of categories of patients to which the patient belongs, wherein the patient is assigned as belonging to one or more of the categories of patients based on the patient-specific data;
   when the patient is eligible for the personalized assistance for adhering to the prescribed therapeutics, calculate an amount of the personalized assistance;
   update the reimbursement schedule to reflect the amount of the personalized assistance available to the patient for adhering to the prescribed therapeutics; and
   forward the updated reimbursement schedule to the pharmacy computing device.

8. The system of claim 7, wherein a patient authorization to use the patient-specific data is received from the pharmacy computing device before comparing the patient-specific data with the structured communications.

9. The system of claim 8, further to transmit a prompt to the pharmacy computing device to prompt the patient to provide the patient authorization.

10. The system of claim 7, wherein the patient-specific data include geographic information regarding the patient.

11. A non-transitory computer readable medium that includes instructions which, when executed, operate to:
receive a prescription claim from a pharmacy, wherein the prescription claim identifies a patient and a therapeutic;
forward the prescription claim to a prescription benefit manager (PBM);
receive a reimbursement schedule from the PBM, wherein the reimbursement schedule sets forth a copayment amount owed by the patient for the therapeutic;
determine whether the therapeutic is eligible for adherence assistance at the pharmacy;
when it is determined that the therapeutic is eligible for adherence assistance, calculate an amount of assistance; and
update the reimbursement schedule to reflect the amount of assistance available to the patient; and
forward the updated reimbursement schedule to a computing device associated with the pharmacy.

12. The non-transitory computer readable medium of claim 11, wherein the prescription claim received from the pharmacy includes a patient consent to use personal data.

13. The non-transitory computer readable medium of claim 11, wherein the prescription claim received from the pharmacy does not include a patient consent to use personal data, further to:
transmit a consent request to the pharmacy to transmit the patient consent to use the personal data when it is determined that the therapeutic is eligible for adherence assistance;
when the patient consent to use the personal data is received, calculate the amount of assistance based on the personal data; and
when the patient consent to use the personal data is not received, calculate the amount of assistance based on aggregated data.

14. The non-transitory computer readable medium of claim 13, wherein the personal data are used to determine a percentage of Federal Poverty Level for the patient.

15. The non-transitory computer readable medium of claim 13, wherein the personal data include a credit score provided by a credit bureau.

16. The non-transitory computer readable medium of claim 13, wherein the personal data include geography data for the patient.

17. The non-transitory computer readable medium of claim 11, wherein a patient authorization to use patient-specific data is received from a pharmacy computing device before comparing the patient-specific data with structured communications that comprise the prescription claim and the reimbursement schedule.

18. The non-transitory computer readable medium of claim 17, further to transmit a prompt to the pharmacy computing device to prompt the patient to provide a patient authorization.

* * * * *